United States Patent
Bange et al.

(10) Patent No.: US 8,046,079 B2
(45) Date of Patent: *Oct. 25, 2011

(54) IMPLANTABLE MEDICAL DEVICE TELEMETRY WITH HOP-ON-ERROR FREQUENCY HOPPING

(75) Inventors: Joseph E. Bange, Eagan, MN (US); Earle Roberts, Maple Grove, MN (US); Kenneth F. Cowan, Kirkland, WA (US); Mehdi Katoozi, Issaquah, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 920 days.

This patent is subject to a terminal disclaimer.

(21) Appl. No.: 11/685,577

(22) Filed: Mar. 13, 2007

(65) Prior Publication Data

US 2008/0228237 A1 Sep. 18, 2008

(51) Int. Cl.
*A61N 1/08* (2006.01)
(52) U.S. Cl. .............. 607/60; 340/539.12; 128/903; 607/32
(58) Field of Classification Search ........... 607/60; 375/132, 135–136
See application file for complete search history.

(56) References Cited

U.S. PATENT DOCUMENTS

| 5,342,408 A | 8/1994 | deCoriolis et al. |
| 5,394,433 A | 2/1995 | Bantz et al. |
| 5,562,713 A | 10/1996 | Silvian |
| 5,617,871 A | 4/1997 | Burrows |
| 5,729,680 A | 3/1998 | Belanger et al. |
| 5,870,391 A | 2/1999 | Nago |
| 5,887,022 A | 3/1999 | Lee |
| 6,031,863 A | 2/2000 | Jusa et al. |
| 6,088,381 A | 7/2000 | Myers, Jr. |
| 6,130,905 A | 10/2000 | Wakayama |
| 6,434,429 B1 | 8/2002 | Kraus et al. |
| 6,443,891 B1 | 9/2002 | Grevious |
| 6,490,487 B1 | 12/2002 | Kraus et al. |
| 6,535,766 B1 | 3/2003 | Thompson et al. |
| 6,704,346 B1 * | 3/2004 | Mansfield ............. 375/136 |
| 6,763,269 B2 * | 7/2004 | Cox .......................... 607/60 |

(Continued)

FOREIGN PATENT DOCUMENTS

EP 1308184 A2 5/2003

(Continued)

OTHER PUBLICATIONS

PCT Application No. PCT/US2007/069426, International Search Report mailed Dec. 27, 2007, 4 pgs.

(Continued)

*Primary Examiner* — Carl H Layno
*Assistant Examiner* — Luther Behringer
(74) *Attorney, Agent, or Firm* — Schwegman, Lundberg & Woessner, P.A.

(57) ABSTRACT

A telemetry system for data transmission between an implantable medical device and an external system includes a plurality of channels each representing a frequency band within a predetermined frequency range. The data transmission is performed using at least one active channel at any instant. Channel hopping is performed upon detecting an interruption of communication, such that a scan is performed through an array of channels selected from the plurality of channels. If a data frame is not successfully transmitted, it is repeatedly re-transmitted using the current and/or the next active channels until its transmission becomes successful.

20 Claims, 7 Drawing Sheets

U.S. PATENT DOCUMENTS

| | | | |
|---|---|---|---|
| 6,801,807 B2 | 10/2004 | Abrahamson | |
| 6,868,288 B2 | 3/2005 | Thompson | |
| 6,978,181 B1 | 12/2005 | Snell | |
| 7,013,178 B2 | 3/2006 | Reinke et al. | |
| 7,177,700 B1 | 2/2007 | Cox | |
| 7,280,872 B1 | 10/2007 | Mosesov et al. | |
| 7,289,853 B1 | 10/2007 | Campbell et al. | |
| 7,623,922 B2 * | 11/2009 | Bange et al. | 607/32 |
| 7,904,169 B2 | 3/2011 | Bange et al. | |
| 2001/0012955 A1 * | 8/2001 | Goedeke et al. | 607/27 |
| 2002/0039380 A1 * | 4/2002 | Steed et al. | 375/132 |
| 2002/0109621 A1 | 8/2002 | Khair et al. | |
| 2003/0026223 A1 * | 2/2003 | Eriksson et al. | 370/335 |
| 2003/0146835 A1 | 8/2003 | Carter | |
| 2006/0030903 A1 | 2/2006 | Seeberger et al. | |
| 2006/0161223 A1 | 7/2006 | Vallapureddy et al. | |
| 2007/0049983 A1 | 3/2007 | Freeberg | |
| 2007/0260293 A1 | 11/2007 | Carpenter et al. | |
| 2008/0015655 A1 | 1/2008 | Bange et al. | |
| 2008/0015656 A1 | 1/2008 | Bange et al. | |
| 2010/0036463 A1 | 2/2010 | Bange et al. | |

FOREIGN PATENT DOCUMENTS

| | | |
|---|---|---|
| WO | WO-98/19400 A1 | 5/1998 |
| WO | WO-2008/008565 A2 | 1/2008 |
| WO | WO-2008/027655 A1 | 3/2008 |
| WO | WO-2008/112222 A2 | 9/2008 |

OTHER PUBLICATIONS

PCT Application No. PCT/US2007/069426, Written Opinion mailed Dec. 27, 2007, 8 pgs.

Adams, J. T., "An introduction to IEEE STD 802.15.4", *Aerospace Conference, 2006 IEEE Big Sky*, (Mar. 4-11, 2006), 1-8.

Duflot, M., et al., "A Formal Analysis of Bluetooth Device Discovery", *International Journal on Software Tools for Technology Transfer*, 8(6), (Jul. 5, 2006), 621-632.

"U.S. Appl. No. 11/456,942, Response filed Nov. 18, 2008 to Non-Final Office Action mailed Aug. 18, 2008", 10 pgs.

"U.S. Appl. No. 11/456,942 Advisory Action mailed May 7, 2009", 6 pgs.

"U.S. Appl. No. 11/456,942, Final Office Action mailed Mar. 10, 2009", 15 pgs.

"U.S. Appl. No. 11/456,942, Notice of Allowance mailed Jul. 17, 2009", 13 pgs.

"U.S. Appl. No. 11/456,942, Response filed May 4, 2009 to Final Office Action mailed Mar. 10, 2009", 9 pgs.

"U.S. Appl. No. 11/456,942, Supplemental Amendment and Response filed Jun. 4, 2009 to Final Office Action mailed Mar. 10, 2009 and Advisory Action mailed May 7, 2009", 10 pgs.

"U.S. Appl. No. 11/456,942, Non-Final Office Action mailed Aug. 18, 2008", 15 pgs.

"International Application Serial No. PCT/US2008/003216, International Search Report mailed Sep. 12, 2008", 4 pgs.

"International Application Serial No. PCT/US2008/003216, Written Opinion mailed Sep. 12, 2008", 8 pgs.

"Australian Application Serial No. 2008226849, Examiner Report mailed Jun. 15, 2010", 2 pgs.

"European Application Serial No. 07811917.9, Office Action Mailed Oct. 28, 2009", 4 pgs.

"Australian Application Serial No. 2008226849, Request to Amend a Complete Specification and First Statement of Proposed Amendments filed Jan. 6, 2011", 11 pgs.

"U.S. Appl. No. 12/579,092, Notice of Allowance mailed Sep. 14, 2010", 8 pgs.

"U.S. Appl. No. 12/579,092, Notice of Allowance mailed Oct. 20, 2010", 8 pgs.

"European Application Serial No. 07811917.9, Response filed Apr. 22, 2010 to Office Action mailed Oct. 28, 2009", 18 pgs.

"European Application Serial No. 08726709.2, Office Action mailed Jul. 23, 10", 6 pgs.

"European Application Serial No. 08726709.2, Office Action Response filed Nov. 26, 2010", 10 pgs.

"European Application Serial No. 07811917.9, Office Action mailed Mar. 9, 2011", 4 pgs.

* cited by examiner

HOP ON ERROR FREQUENCY HOPPING STATE DIAGRAM PG SIDE

IMPLANTABLE MEDICAL DEVICE TELEMETRY WITH HOP-ON-ERROR FREQUENCY HOPPING

CROSS-REFERENCE TO RELATED APPLICATION

This application is related to commonly assigned, U.S. patent application Ser. No. 11/456,942, entitled "IMPLANTABLE MEDICAL DEVICE TELEMETRY WITH PERIODIC FREQUENCY HOPPING," filed on Jul. 12, 2006, now issued as U.S. Pat. No. 7,623,922, which is hereby incorporated by reference in its entirety.

TECHNICAL FIELD

This disclosure relates generally to implantable medical devices and, more particularly, to systems for communicating with implantable medical devices.

BACKGROUND

Implantable medical devices (IMDs) include devices implanted in the human body to provide medical treatment. Examples of such implantable medical devices include cardiac rhythm management (CRM) devices, neural stimulators, neuromuscular stimulators, drug delivery devices, and biological therapy devices. A device exterior to the human body, called a programmer, is used to program an IMD.

Some programmers and IMDs communicate via radio frequencies (RF) telemetry using a wireless electrical connection. The quality of the wireless communication between the programmer and the IMD, whether in an operating room, an intensive care facility, a patient follow-up clinic, or home monitoring situation, may be limited by causes such as interference from other RF sources and large transmission distance. Improved telemetry systems for communication with IMDs are needed.

SUMMARY

The above-mentioned problems and others not expressly discussed herein are addressed by the present subject matter and will be understood by reading and studying this specification.

A telemetry system for data transmission between an implantable medical device and an external system includes a plurality of channels each representing a frequency band within a predetermined frequency range. The data transmission is performed using at least one active channel at any instant. Channel hopping is performed upon detecting an interruption of communication, such that a scan is performed through an array of channels selected from the plurality of channels. If a data frame is not successfully transmitted, it is repeatedly re-transmitted using the current and/or the next active channels in a channel selection sequence until its transmission becomes successful.

In one embodiment, a system includes an implantable medical device and an external system communicating with each other via telemetry. The implantable medical device includes a therapy module and an implant telemetry module. The external system includes a programming module and an external telemetry module. The implant telemetry module and the external telemetry module each include a telemetry circuit that includes an antenna, a transceiver, and a telemetry controller. The transceiver includes a plurality of channels each representing a predetermined frequency band for data transmission between the implantable medical device and the external system. The telemetry controller controls data transmission and channel hopping during synchronous and asynchronous scan modes. The channel hopping includes detecting an interruption of communication on a first frequency, scanning a subset of available communication frequencies for a response from the implantable medical device, and resuming communication with the implantable medical device after receiving a response, on a second frequency on which the response was received.

In one embodiment, a method for data transmission between an implantable medical device and an external system is provided. The embodiment includes communicating wirelessly with an implantable medical device using a first frequency until a problem is detected that interrupts communication on the first frequency. The embodiment also includes scanning a subset of available communication frequencies for a response from the implantable medical device. The embodiment further includes resuming communication with the implantable medical device after receiving a response, on a second frequency on which the response was received.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present subject matter refers to subject matter in the accompanying drawings which show, by way of illustration, aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Various embodiments of the present subject matter are related to a communication system between an external programmer recorder (programmer or PRM) and an implantable medical device (IMD) such as a pulse generator (PG). The disclosed communication system uses hop-on-error frequency hopping over a set of M-ary radio frequencies (RF). The PRM and IMD change frequencies (or channels) upon detection of a problem with communication on the current frequency. The system is designed to recover from a long period of disruption in communication by the PRM scanning the frequencies looking for a response from the IMD on a subset of the hopping frequencies. To maintain synchronization of frequency changes between the PRM and the IMD, the PRM is designed to set or reset the hopping clock internal to the IMD.

While the application in a cardiac rhythm management (CRM) system is specifically discussed as an example, the present subject matter is applicable to any RF telemetry between an implantable medical device and an external system. The implantable medical device can be any implantable medical device capable of communicating with an external system or device via RF telemetry.

Figure 1:
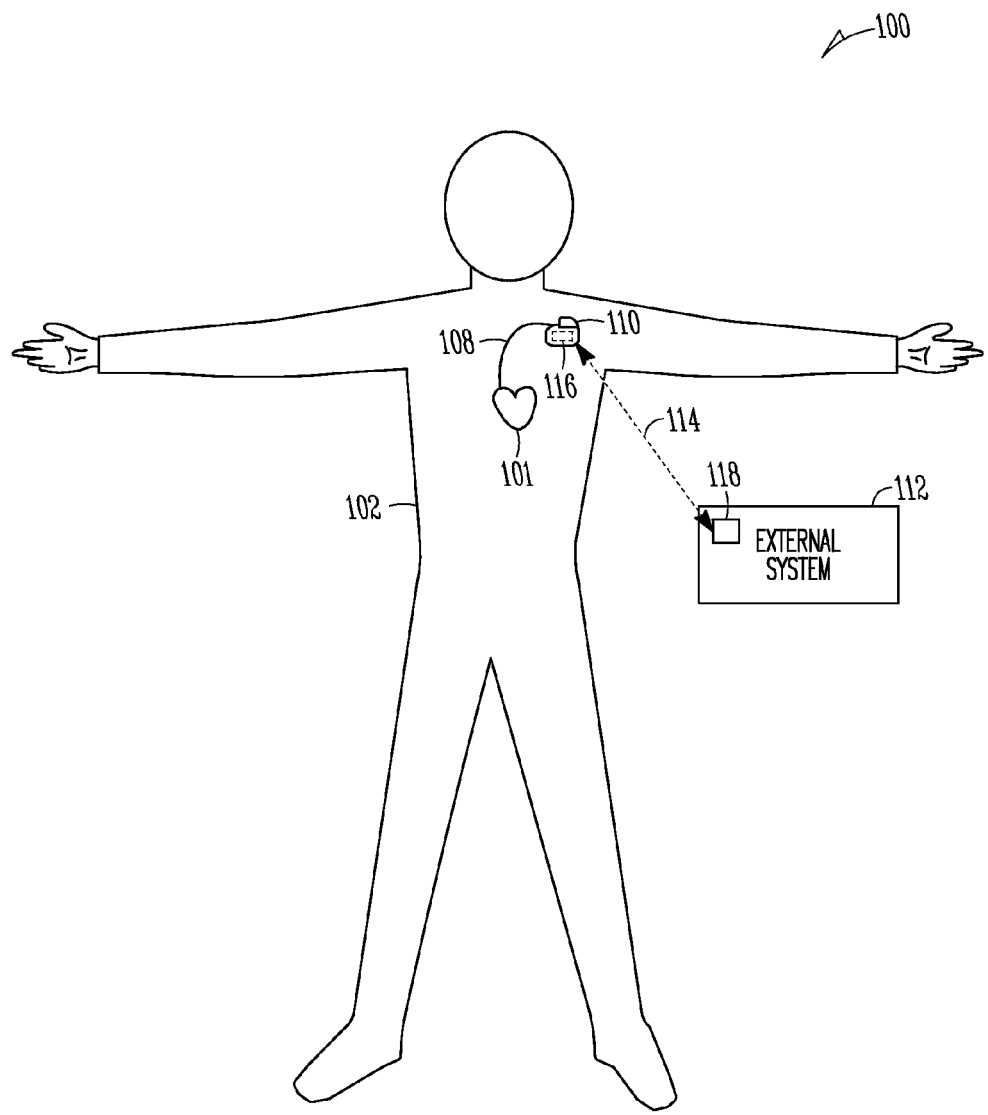
FIG. 1 is an illustration of an embodiment of an implantable medical device (IMD) system and portions of an environment in which the system is used.

FIG. 1 is an illustration of an embodiment of an IMD system 100 and portions of an environment in which system 100 is used. System 100 includes an implantable medical device 110 and an external system 112. In the illustrated embodiment, after being implanted into a patient's body 102, implantable medical device 110 is coupled to the patient's heart 101 through a lead system 108. In various embodiments, implantable medical device 110 includes one or more of pacemakers, cardioverter/defibrillators, cardiac resynchronization therapy (CRT) devices, cardiac remodeling control therapy (RCT) devices, neural stimulators, drug delivery systems, biological therapy devices, and patient monitoring devices. External system 112 allows a physician or other caregiver to interact with implantable medical device 110 through a telemetry link 114, which provides for bi-directional data communication between implantable medical device 110 and external system 112.

Telemetry link 114 provides for data transmission from implantable medical device 110 to external system 112. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 114 also provides for data transmission from external system 112 to implantable medical device 110. This includes, for example, programming implantable medical device 110 to acquire physiological data, programming implantable medical device 110 to perform at least one self-diagnostic test (such as for a device operational status), and programming implantable medical device 110 to deliver at least one therapy.

In one embodiment, telemetry link 114 is a far-field RF telemetry link. A far-field, also referred to as the Fraunhofer zone, refers to the zone in which a component of an electromagnetic field produced by the transmitting electromagnetic radiation source decays substantially proportionally to $1/r$, where r is the distance between an observation point and the radiation source. Accordingly, far-field refers to the zone outside the boundary of $r=\lambda/2\pi$, where $\lambda$ is the wavelength of the transmitted electromagnetic energy. In one embodiment, a communication range of telemetry link 114 (a distance over which data is capable of being wirelessly communicated) is at least ten feet but can be as long as allowed by the communication technology utilized. Unlike an inductive telemetry link using a coil placed near implantable medical device 110, attached to the patient, and electrically connected to external system 112 with a cable, using telemetry link 114 frees the patient from any physical restraints caused by the coil and the cable and allows external system 112 to be placed away from the sterile field during an operation such as the implantation of implantable medical device 110.

Telemetry link 114 is supported by an implant telemetry module 116 of implantable medical device 110 and an external telemetry module 118 of external system 112. Implant telemetry module 116 and external telemetry module 118 form a frequency agile telemetry system that includes a plurality of channels for data transmission. These channels each represent a frequency band within a predetermined frequency range. The telemetry system performs channel hopping upon detection of a problem that interrupts communication. The channel hopping is performed synchronously such that implant telemetry module 116 and external telemetry module 118 use the same frequency band for data transmission between them. In one embodiment, implant telemetry module 116 functions as a slave device and external telemetry module 118 functions as a master device. The master device maintains the synchronous channel hopping. When the channel hopping becomes asynchronous, the master device controls a resynchronization process to restore the synchronous channel hopping.

The bi-directional data communication between implantable medical device 110 and external system 112 includes transmission of data frames each being a logic unit of data including a header, a payload, and a trailer. In one embodiment, the header includes a "comma," which includes a unique set of bits for signaling the beginning of receipt of a frame. A lack of comma, or failure to receive the comma, indicates a failure to receive a frame. The payload includes the data block being transmitted. The trailer includes a cyclic redundancy check (CRC) value having a value generated by a transmitter. A receiver receives that CRC value and also recalculates the CRC value based on the received data block and compares the result to the received CRC value in the trailer. The data is deemed to be correctly transmitted if the recalculated CRC value matches the received CRC value. A CRC error refers to a mismatch between the recalculated CRC value and the received CRC value. Depending on the specific communication formats, the header and the trailer each include additional information for flagging, control of data recovery, and/or synchronization between implant telemetry module 116 and external telemetry module 118. In various embodiments, data frame exchange errors, such as comma errors and CRC errors, indicate a need for re-transmission of the same data frame using the current and/or next active channels.

In one embodiment, external system 112 includes a programmer. In another embodiment, external system 112 includes a patient management system including an external device, a telecommunication network, and one or more remote devices. The external device is placed within the vicinity of implantable medical device 110 and includes external telemetry module 118 to communicate with implantable medical device 110 via telemetry link 114. The one or more remote devices are in one or more remote locations and communicate with the external device through the telecommunication network, thus allowing the physician or other caregiver to monitor and treat the patient from a distant location and/or allowing access to various treatment resources from the one or more remote locations.

Figure 2:
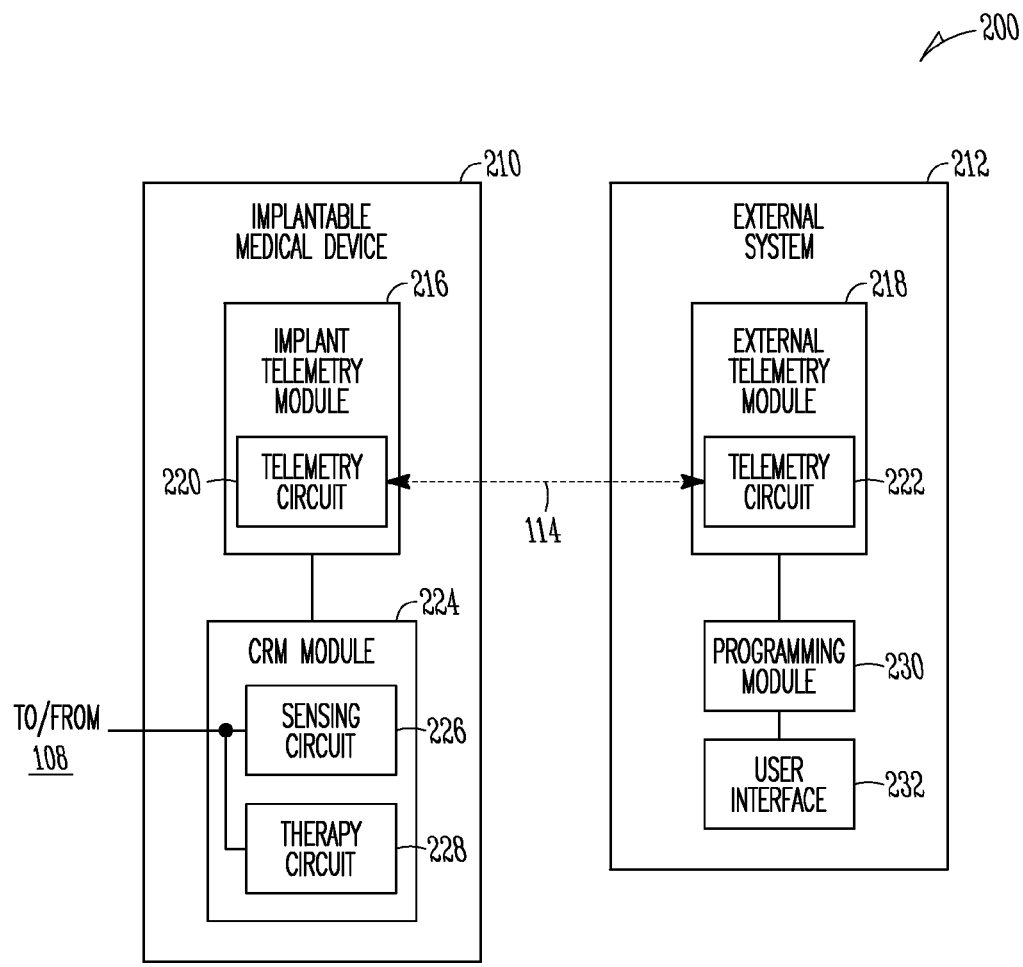
FIG. 2 is a block diagram illustrating an embodiment of a circuit of the IMD system.

FIG. 2 is a block diagram illustrating an embodiment of a circuit of an IMD system 200, which is an embodiment of IMD system 100. System 200 includes an implantable medical device 210, an external system 212, and telemetry link 114 providing for communication between implantable medical device 210 and external system 212.

Implantable medical device 210 is an embodiment of implantable medical device 110 and includes an implant telemetry module 216 and a CRM module 224. Other types of therapy modules could be used without departing from the scope of this disclosure. CRM module 224 includes a sensing circuit 226 that senses one or more physiological signals and a therapy circuit 228 that delivers one or more cardiac therapies. In various embodiments, therapy circuit 228 includes one or more of a pacing circuit, a cardioversion/defibrillation circuit, CRT circuit, RCT circuit, and any other circuit that delivers a cardiac therapy. In one embodiment, therapy circuit 228 delivers cardiac electrical stimulation pulses such as pacing and cardioversion/defibrillation pulses. In various embodiments, CRM module 224 further includes one or more of a drug delivery device and a biologic therapy device.

External system 212 is an embodiment of external system 112 and includes an external telemetry module 218, a programming module 230, and a user interface 232. Programming module 230 allows for processing of data transmitted from implantable medical device 210 via telemetry link 114 and programming of implantable medical device 210 by transmitting instructions via telemetry link 114. User interface 232 allows the physician or other caregiver to observe and analyze physiological signals and device operation data transmitted from implantable medical device 210 and to adjust the operation of implantable medical device 210.

Implant telemetry module 216 includes a telemetry circuit 220. External telemetry module 218 includes a telemetry circuit 222. Telemetry circuits 220 and 222 are discussed in detail below, with reference to FIGS. 4 and 5.

In various embodiments, the system elements, including various modules and circuits, described in this document are implemented by hardware, software, firmware, or any combination thereof. In various embodiments, the circuits or portions thereof described in this document are each an application-specific circuit constructed to perform one or more particular functions, a general-purpose circuit programmed to perform such function(s), or a combination thereof.

Figure 3:
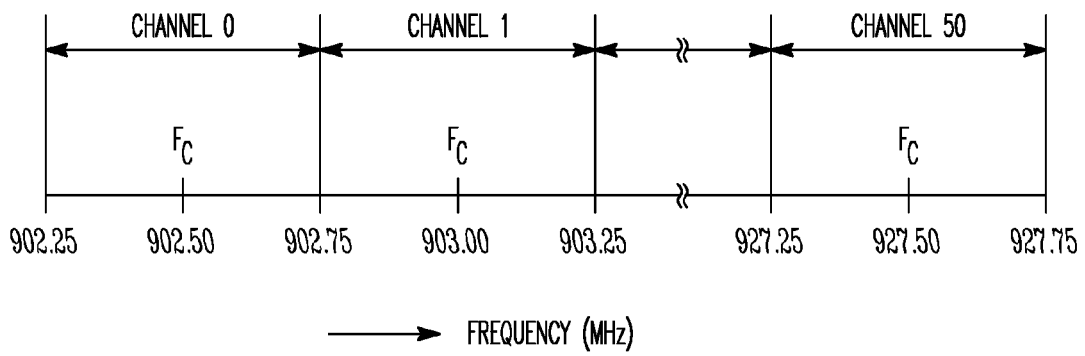
FIG. 3 is an illustration of an embodiment of telemetry channels (frequency bands) for data transmission between an implantable medical device and an external system of the IMD system.

FIG. 3 is an illustration of an embodiment of the plurality of channels for data transmission via telemetry link 114. The channels are distributed over the predetermined frequency range. As illustrated in FIG. 3, an example of the predetermined frequency range is approximately 902.25-927.75 MHz. Each channel has a center (carrier) frequency and a bandwidth of approximately 500 kHz. Thus, the plurality of channels includes 51 channels each having a 500-kHz bandwidth within the frequency range of 902.25-927.75 MHz, within the Industrial, Scientific and Medical (ISM) band of the United States. The center frequency for each channel is approximately the mid-point of the frequency band represented by that channel. In the illustrated embodiment, Channel 0 has a frequency band of 902.25-902.75 MHz and a center frequency of 902.50 MHz, Channel 1 has a frequency band of 902.75-903.25 MHz and a center frequency of 903.00 MHz, and so forth. Other examples of the predetermined frequency range include approximately 863.0-870.0 MHz, within the Short Range Device (SRD) band of the European Union, approximately 402.0-405.0 MHz, within the worldwide Medical Implant Communication Service (MICS) band, and approximately 420.0-430.0 MHz and 440.0-450.0 MHz, within the available bands in Japan.

Figure 4:
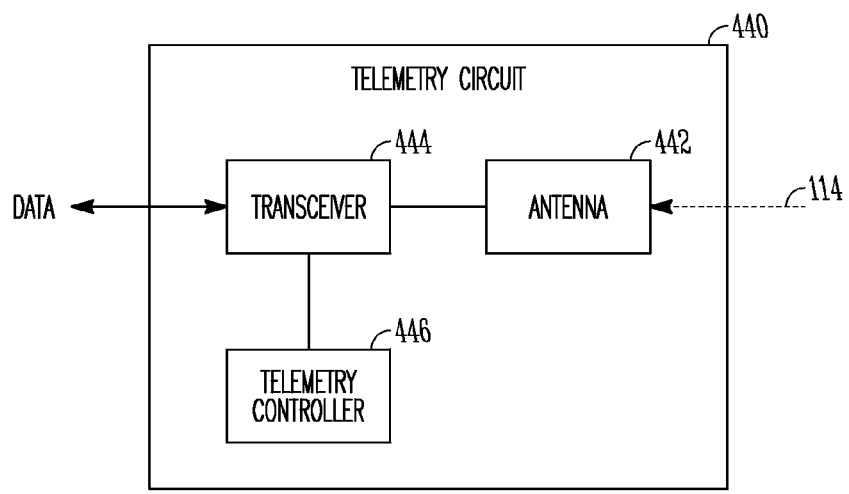
FIG. 4 is a block diagram illustrating an embodiment of a telemetry circuit of the IMD system.

FIG. 4 is a block diagram illustrating an embodiment of a telemetry circuit 440. Telemetry circuit 440 represents an embodiment of telemetry circuit 220 and/or telemetry circuit 222. In various embodiments, telemetry circuit 220 and telemetry circuit 222 each include a telemetry circuit illustrated as telemetry circuit 440 and discussed in this document.

Telemetry circuit 440 includes an antenna 442, a transceiver 444, and a telemetry controller 446. Transceiver 444 transmits and receives data through antenna 442 using at least one active channel during a telemetry session. The active channel is selected from the plurality of channels each representing a predetermined frequency band for data transmission via telemetry link 114. Telemetry controller 446 controls channel hopping, in an embodiment. The embodiment includes communicating wirelessly with an implantable medical device using a first frequency until a problem is detected that interrupts communication on the first frequency. The embodiment also includes scanning a subset of available communication frequencies for a response from the implantable medical device. The embodiment further includes resuming communication with the implantable medical device after receiving a response, on a second frequency on which the response was received.

The channel hopping includes selecting the active channel from the plurality of channels. After an active channel is selected, telemetry controller 446 controls the data transmission using the active channel during a synchronous scan mode, during which the channel hopping in the external system and the channel hopping in the implantable medical device are synchronous. If the channel hopping in the external system and the channel hopping in the implantable medical device become asynchronous, telemetry controller 446 starts an asynchronous scan mode. During the asynchronous scan mode, telemetry controller 446 restores the synchronization of the channel hopping in the external system and the channel hopping in the implantable medical device.

Figure 5:
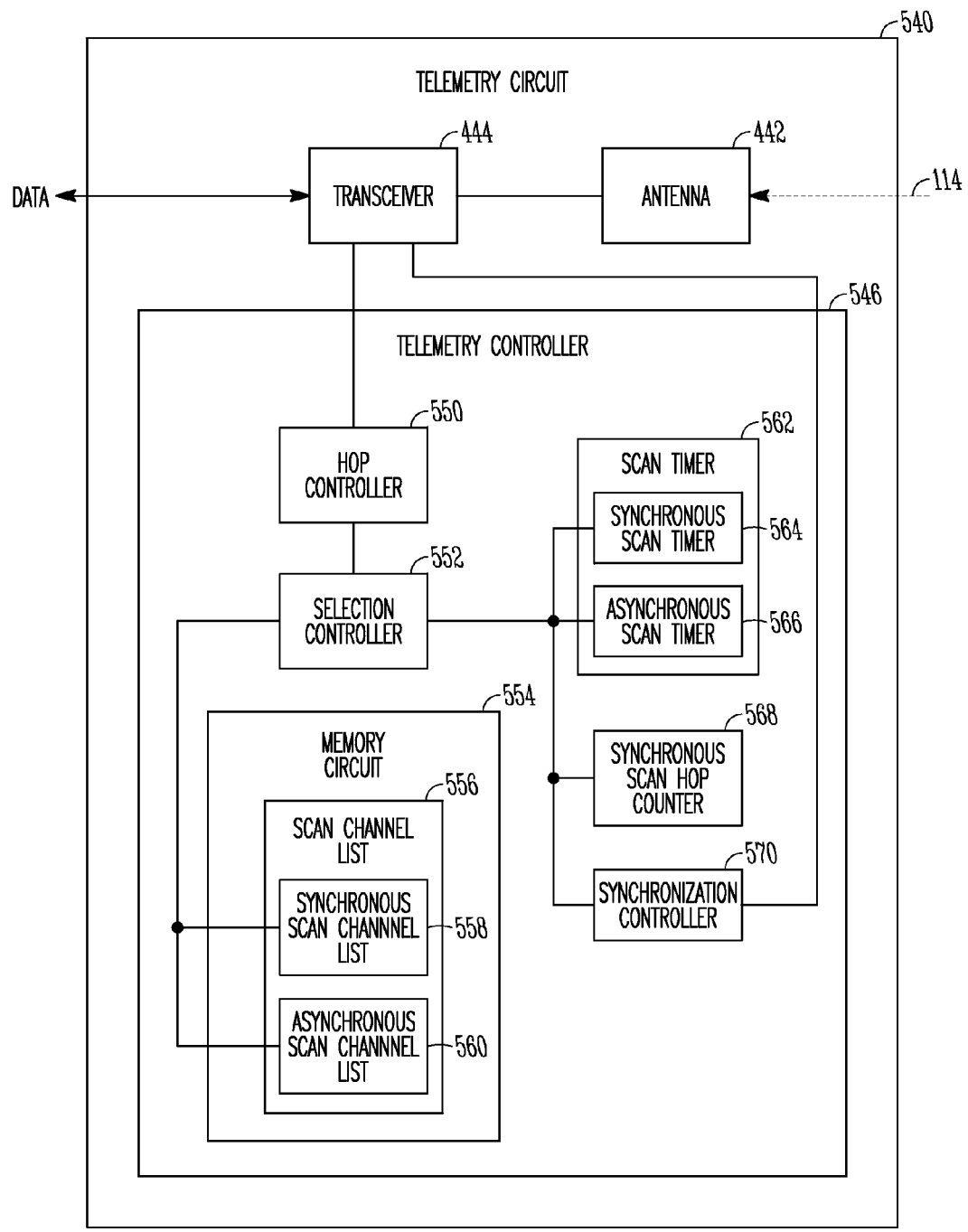
FIG. 5 is a block diagram illustrating an embodiment of the telemetry circuit.

FIG. 5 is a block diagram illustrating an embodiment of a telemetry circuit 540, which is an embodiment of telemetry circuit 440. Telemetry circuit 540 includes antenna 442, transceiver 444, and a telemetry controller 546. Telemetry controller 546 includes a hop controller 550, a selection controller 552, a memory circuit 554, a scan timer 562, a synchronous scan hop counter 568, and a synchronization controller 570.

Selection controller 552 produces channel selection commands each specifying a channel in the scan channel list when a scan timer escape interval expires. Hop controller 550 controls a channel hopping in response to each of the channel selection commands. The channel hopping makes the channel specified in the each of the channel selection commands the active channel for the data transmission via telemetry link 114. During the synchronous scan mode, selection controller 552 produces each of the channel selection commands when a synchronous scan timer escape interval expires. The channel selection commands specify the channels in a synchronous hopping sequence. During the asynchronous scan mode, selection controller 552 produces each of the channel selection commands when an asynchronous scan timer escape interval expires. The channel selection commands specify the channels in an asynchronous hopping sequence.

Memory circuit 554 stores a scan channel list 556, which is the scan channel list including the channels specified in the channel selection commands. Scan channel list 556 includes a synchronous scan channel list 558 and an asynchronous scan channel list 560. Synchronous scan channel list 558 includes a first array of channels listed in the synchronous hopping sequence. Asynchronous scan channel list 560 includes a second array of channels listed in the asynchronous hopping sequence. Selection controller 552 produces the channel selection commands specifying the channels in synchronous scan channel list 558 during the synchronous scan mode, and produces the channel selection commands specifying the channels in asynchronous scan channel list 560 during the asynchronous scan mode. In one embodiment, the first array of channels including all the channels of the plurality of channels. In another embodiment, the first array of channels includes preferred channels selected from the plurality of channels. In one embodiment, the second array of channels is a subset of the first array of channels.

Scan timer 562 times the scan timer escape interval. Scan timer 562 includes a synchronous scan timer 564 and an asynchronous scan timer 566. Synchronous scan timer 564 times the synchronous scan timer escape interval during the synchronous scan mode. In one embodiment, the synchronous scan timer escape interval is between approximately 10 and 250 ms. Asynchronous scan timer 566 times the asynchronous scan timer escape interval during the asynchronous scan mode. In one embodiment, the asynchronous scan timer escape interval of external telemetry module 218 has a length allowing external telemetry module 218 to hop through all channels of its asynchronous scan channel list 560 during each asynchronous scan timer escape interval of implant telemetry module 216. This allows external telemetry module 218 to scan all the channels in its asynchronous scan channel list 560 against each channel of the asynchronous scan channel list 560 of implant telemetry module 216 until the channels are matched in the external telemetry module 218 and implant telemetry module 216.

Synchronous scan hop counter 568 counts a synchronous scan hop count during the synchronous scan mode. When the synchronous scan hop count reaches a predetermined maximum hop count, synchronous scan hop counter 568 starts the asynchronous scan mode. The synchronous scan hop count is incremented each time when the synchronous scan timer escape interval expires and is reset by a signal indicative of successful data transmission. In other words, when the number of channels attempted to transmit the same data frame without success reaches the predetermined maximum hop count, synchronous scan hop counter 568 starts the asynchronous scan mode.

During the synchronous scan mode, synchronization controller 570 maintains the synchronization of the channel hopping in external telemetry module 218 and implant telemetry module 216. During the asynchronous scan mode, synchronization controller 570 restores the synchronization of the channel hopping in external telemetry module 218 and implant telemetry module 216 to re-enter the synchronous scan mode.

Figure 6:
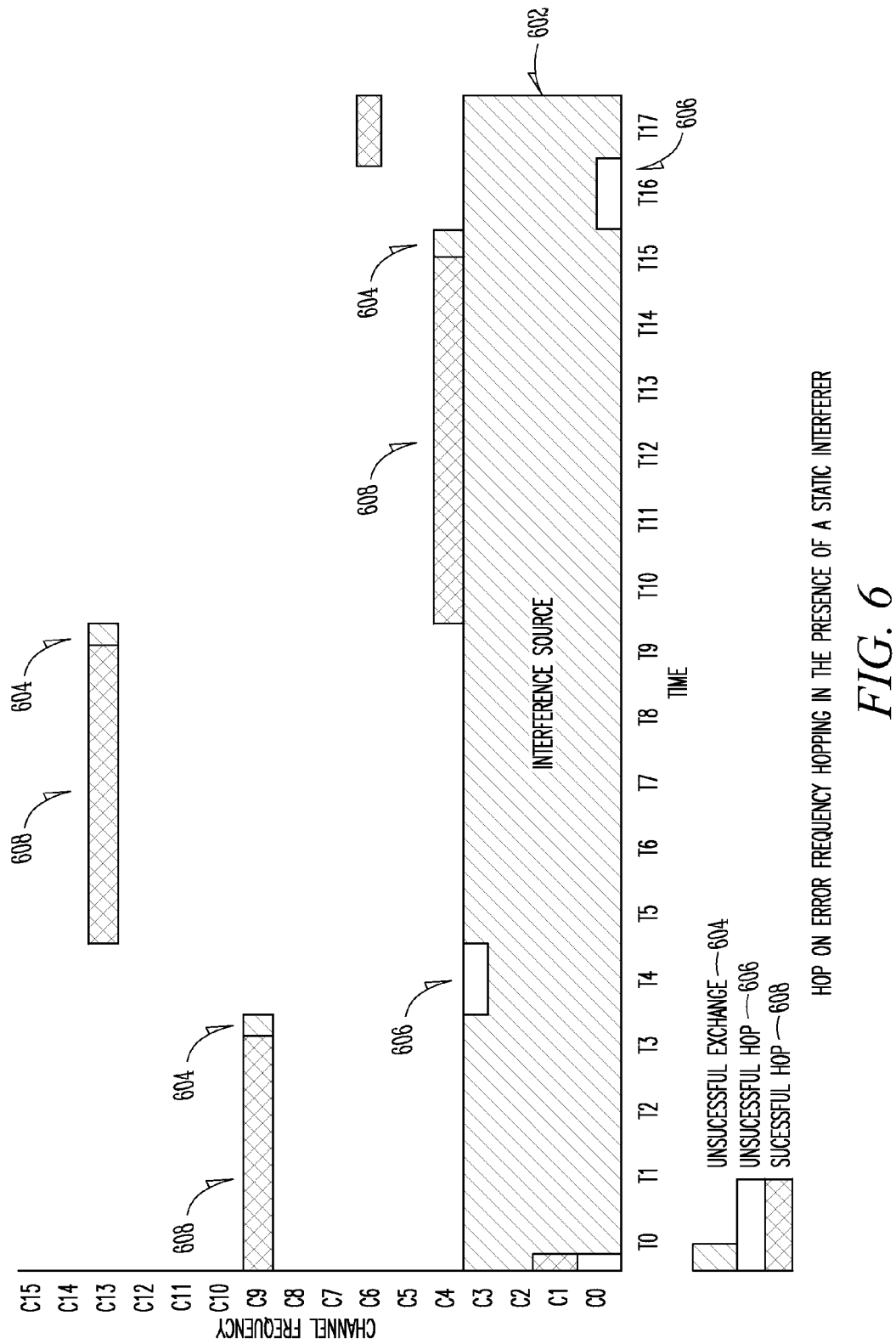
FIG. 6 is a graphical diagram of an example of hop-on-error frequency hopping, according to an embodiment.

FIG. 6 illustrates a graphical diagram of an example of hop-on-error frequency hopping, according to an embodiment. The shaded area 602 represents a static interferer. In the depicted frequency hopping implementation in the presence of the static interferer, some channels provide good performance while others do not. Unsuccessful exchanges are shown at 604, unsuccessful hops at 606 and successful hops at 608, in the depicted embodiment.

The term "physical channel" refers to a channel in terms of its center frequency, bandwidth, and other physical attributes. The IMD hardware is provided with the programming information associated with each channel that might be tuned to during a communication session. The programming information for each of the physical channels is stored into an array known as the physical channel list. The physical channel attributes can then be reference using an index into the physical channel list. This index is referred to as the "logical channel."

The Scan Channel List is used to hold an array of logical channels. The logical channels may appear in any order within the Scan Channel List. The order that the logical channels appear in the Scan Channel List sets the order in which frequency hopping occurs. From the Scan Channel List, two sub-lists, the synchronous scan list and the asynchronous scan list are generated using bit masks that enable and disable specific channels. According to various embodiments, the Scan Channel List is 64 entries long. The List may be longer or shorter, without departing from the scope of this disclosure. Using a 64 entry List, the synchronous channel mask and the asynchronous channel mask are both 64 bits in size, with the least significant bit (LSB), D0, being mapped to Scan Channel List index 0, and the most significant bit (MSB), D63, being mapped to Scan Channel List index 63. The actual number of channels in the list is set by the available bandwidth for use divided by the bandwidth required for a single channel.

According to various embodiments, hardware resources used in implementing frequency hopping systems include a command to select the current channel (for communication between the IMD and the PRM) and to set the synchronous scan timer escape interval. According to an embodiment, this command is referred to as the SetPrimaryChannel command. The hardware resources also include a synchronous scan timer, according to various embodiments. The synchronous scan timer is used to time how long the PRM and IMD stay on a channel while in synchronous mode. On expiration of the timer, the PRM and the IMD will change to the next channel in the synchronous list and increment a synchronous scan hop counter. The synchronous scan timer intervals are the same on both the PRM and the IMD so that the two sides synchronously hop channels. According to various embodiments, the hardware resources further include a synchronous scan hop counter used to break out to the synchronous scan mode and enter asynchronous scan mode. The counter is started when synchronous scan mode is entered. Each successful transmission or reception of an acknowledge (ACK) frame resets this counter to zero. On expiration of the synchronous scan timer, this counter is incremented. When this counter reaches the threshold maximum synchronous scan hop count (a programmable parameter), the PRM and the IMD enter asynchronous scan mode. The hardware resources also include an asynchronous scan timer, according to varying embodiments. This timer is used to time how long the PRM and the IMD stay on a channel when trying to establish a new frequency channel between the PRM and the IMD while in asynchronous mode. This timer is idle until the synchronous scan hop counter reaches the max synchronous scan hop count, and asynchronous scan mode is entered. On expiration of the timer, the PRM and the IMD will change to the next channel in the asynchronous list. The timer is set to different intervals in the PRM and the IMD such that the PRM hops through all channels in the asynchronous scan list in the same time interval that the IMD hops only one frequency.

According to various embodiments, a method is provided for synchronizing frame exchanges with channel changes in hop-on-error mode. A SCAN frame is transmitted by the PRM to the IMD, which responds with a SCAN frame upon receipt. According to an embodiment, the PRM and the IMD use the transmission or valid reception of an ACK frame as the trigger to reset a primary channel timer. As long as communications are working successfully, both the PRM and the IMD will be resetting the primary channel timer at a polling rate of 100 milliseconds (ms), or less if more date is ready to transfer. When communications break down, and no ACK frames are transmitted or received, the primary channel timer will expire, putting the PRM and the IMD into the synchronous scan mode. For the IMD, entering a synchronous scan mode causes the IMD to reset and enable the synchronous scan timer and clear the synchronous scan hop count. The IMD then hops to the next channel in the synchronous scan list. Assuming the IMD is on channel 0 (C0) of the synchronous scan list prior to the primary channel timer expiring, in an embodiment, the IMD will hop to channel 1 (C1). The IMD will continue to hop channels on expiration of the synchronous scan timer until it successfully transmits or receives an ACK frame. According to an embodiment, the PRM, when entering synchronous scan mode, will poll a list of 9 channels including the next 9 channels from the synchronous scan list. The existing channel is not on the list, as it has failed for several tens of milliseconds and is unlikely to produce a valid exchange in the near future. For each of the 9 channels in this embodiment, the PRM will send the SCAN frame and listen for a SCAN frame response from the IMD.

If a SCAN frame is received from the IMD by the PRM, the PRM take the following steps. First, the PRM will have identified which frequency the IMD is using, so the scan list is modified to make this frequency/channel the first on the list, and the remaining part of the list is filled in with the 8 channels that follow, according to an embodiment. The PRM then attempts a normal data exchange with the IMD, either inbound (forward) or outbound (reverse). If this normal data exchange is completed, an ACK frame would have been transmitted or received, the primary channel timer reset and enabled, the synchronous timer disabled, and both the PRM and the IMD return to normal operation mode. If the normal data exchange fails, then the synchronous scan resumes from the current channel.

According to various embodiments, if no valid SCAN frame response is received by the PRM, the SCAN frame will by retried on the other diversity antenna at the same frequency. After two attempts, the PRM will go to the next frequency on the list and again try the SCAN frame on both antennas. Since the SCAN frame is a control frame, a simple transmit/receive pair will take approximately 1.36 ms (15 bytes @ 250 kbps takes 480 μs is to transmit, and two frames with turn around of about 200 μs then take 1.36 ms). Therefore, the two attempts on each frequency will allow 9 channels to be tried in one synchronous scan timer period, which is nominally programmed to 25 ms, that the IMD is listening on a single frequency (as the synchronous scan timer interval is 25 ms/1.36 ms per scan=18.38 scans, with 2 scans per channel that is 9 channels). The PRM modifies its list of channels to keep pace with the IMD. A number of scenarios, discussed below, detail when the PRM begins to modify the scan list. Once started, the PRM modifies the scan list synchronous timer expiration by dropping the first channel in the list and adding the next channel from the synchronous scan list to the end of the scan. For example, the first modification may be to drop C1 and add C10, so the new scan list will be C2 to C10. 25 milliseconds later, the PRM may drop C2 and add C11, to form a scan list of C3 to C11. By continuing in this manner, the PRM keeps a window of scanned channels around where the IMD channel is most likely to be. This pattern is continued until a new channel is found or the Synchronous Scan Hop Count Max is reached. According to an embodiment, if the Synchronous Scan Hop Count Max is reached, the PRM and IMD switch to the asynchronous scan list. An asynchronous scan list of 9 channels is used, and the IMD continues to hop channels at the nominal 25 ms Asynchronous Scan Timer period, according to various embodiments. The PRM continues scanning in the same manner, but the scan lists are shorter and are the same for the PRM and the IMD, removing the possibility that the PRM is not scanning the same frequency as the IMD.

Figure 7:
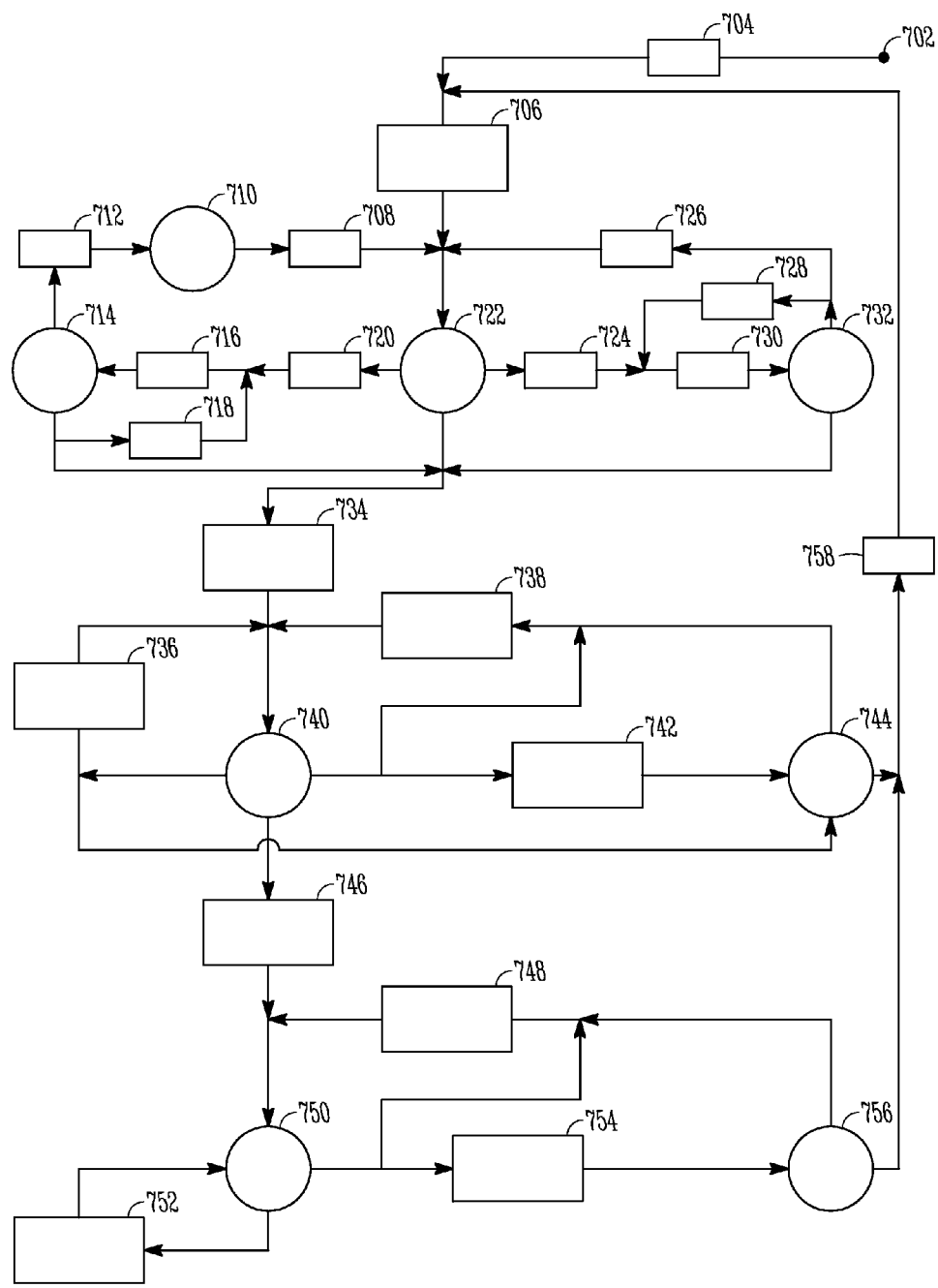
FIG. 7 is a state diagram illustrating an embodiment of frequency hopping in an external system communicating with an IMD.
Figure 8:
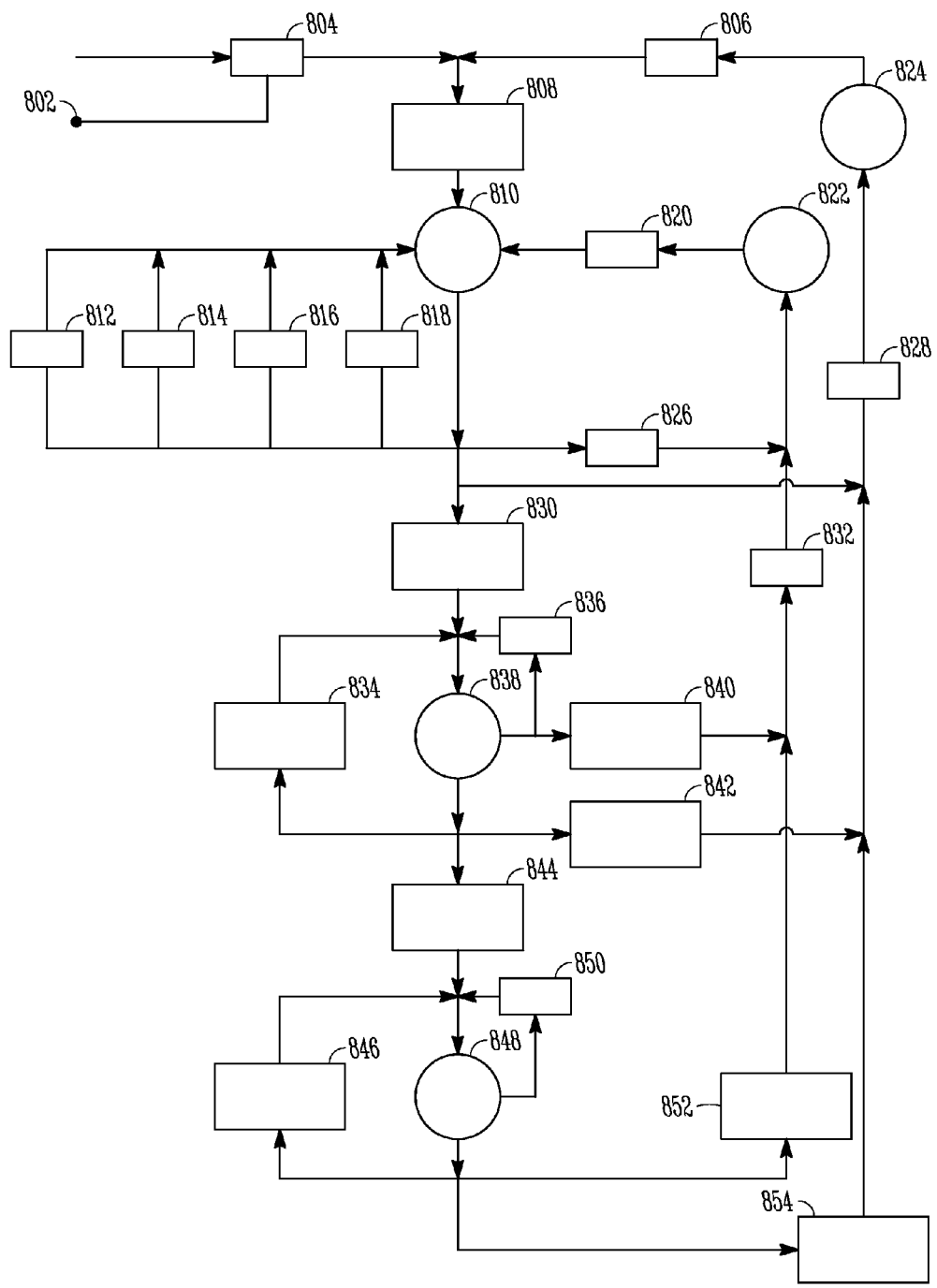
FIG. 8 is a state diagram illustrating an embodiment of frequency hopping in the IMD communicating with the external system.

FIG. 7 illustrates a state diagram of hop-on-error frequency hopping from the PRM, or external system, perspective, according to an embodiment. FIG. 8 illustrates a state diagram of hop-on-error frequency hopping from the IMD, or PG, perspective, according to an embodiment. The following is a list of description of states and acts represented by reference numbers in FIGS. 7 and 8:

FIG. 7 (the external system):
702:
 Starting the hop-on-error frequency hopping mode.
704:
 Wake-up or mode change from a fixed-frequency mode
706:
 Stop synchronous scan timer;
 Stop asynchronous scan timer;
 Conditionally set primary timer;
 Start primary scan timer.
708:
 ACK (ACKnowledge frame) transmission completed;
 Clear primary scan timer.
710:
 ACK transmission.
712:
 DS (Data Send frame) received;
 Transmit ACK.
714:
 Primary wait for DS.
716:
 Transmit CTS (Clear To Send frame);
 Set DS timeout.
718:
 DS timeout.
720:
 Reverse exchange request.
722:
 Primary channel mode.
724:
 Forward exchange request.
726:
 ACK received;
 Clear primary scan timer.
728:
 ACK timeout.
730:
 Transmit DS frame;
 Set ACK timeout.
732:
 Wait for ACK.
734:
 Primary timer expires;
 Stop primary timer;
 Cancel DS/ACK timeout;
 Create short synchronous scan list;
 Switch to next synchronous channel;
 Start synchronous scan timer;
 Transmit SCAN frame.

736:
  Synchronous scan timer expires;
  Modify short synchronous scan list;
  Switch to first synchronous channel;
  Transmit SCAN frame.
738:
  Response timeout;
  Use alternative antenna;
  Hop to the next channel on the synchronous scan channel list (after using all antennas);
  Transmit SCAN frame.
740:
  Synchronous scan mode.
742:
  SCAN response frame received;
  Transmit NODATA (frame indicating NO DATA to send) or SPC (Set Primary [i.e., active] Channel frame);
  Set response timeout.
744:
  Waiting for response in the synchronous scan mode.
746:
  Max synchronous scans reached;
  Stop synchronous scan timer;
  Set channel list to asynchronous list;
  Switch to next asynchronous channel;
  Set scan response timer;
  Start scan response timer;
  Transmit SCAN frame.
748:
  Response timeout;
  Use alternative antenna;
  Hop to the next channel on the asynchronous scan channel list (after using all antennas);
  Transmit SCAN frame.
750:
  Asynchronous scan mode.
752:
  Scan response timer expires;
  Switch to next asynchronous channel;
  Transmit SCAN frame.
754:
  SCAN response frame received;
  Transmit NODATA or SPC;
  Set response timeout.
756:
  Waiting for response in the asynchronous scan mode.
758:
  Response received.
FIG. 8 (the implantable medical device):
802:
  Starting the hop-on-error frequency hopping mode.
804:
  Wake-up or mode change from a fixed-frequency mode.
806:
  SPC transmission completed.
808:
  Set primary timer;
  Set primary channel;
  Start primary timer.
810:
  Primary channel mode.
812:
  RRTS (Request for Request to Send) received;
  Transmit RTS (Request to Send)/NODATA.
814:
  RTS received;
  Transmit CTS.
816:
  CTS received;
  Transmit DS/NODATA.
818:
  ACK received;
  Clear primary timer.
820:
  ACK transmission completed;
  Clear primary timer.
822:
  Transmitting ACK.
824:
  Transmit SPC response.
826:
  DS, DSMD (Data Send with More Data frame), or NODATA received;
  Transmit ACK or NACK (No ACKnowledgement frame, indicating that a message is received but unable to process at the moment).
828:
  SPC received;
  Transmit SPC response.
830:
  Primary timer expired;
  Stop primary timer;
  Clear hop count;
  Change to next synchronous channel;
  Start synchronous scan timer;
832:
  NODATA frame received;
  Transmit ACK.
834:
  Synchronous scan timer expired;
  Increment the synchronous scan hop count;
  Hop to the next channel on the synchronous scan channel list;
  Start synchronous scan timer.
836:
  SCAN received;
  Transmit SCAN.
838:
  Synchronous scan mode.
840:
  NODATA frame received;
  Stop the synchronous scan timer;
  Clear primary timer;
  Start primary timer.
842:
  SPC received;
  Stop the synchronous scan timer;
  Set scan channel list to the synchronous scan channel list
844:
  Maximum synchronous hop count reached;
  Stop the synchronous scan timer;
  Set scan channel list to the asynchronous scan channel list;
  Hop to the next channel on the asynchronous scan channel list.
  Clear the asynchronous scan timer;
  Start the asynchronous scan timer;
846:
  Asynchronous scan timer escape interval expired;
  Hop to the next channel on the asynchronous scan channel list.

848:
  Asynchronous scan mode.
850:
  SCAN received;
  Transmit SCAN.
852:
  NODATA frame received;
  Stop the asynchronous scan timer;
  Set scan channel list to the synchronous scan channel list;
  Clear primary timer;
  Start primary timer.
854:
  SPC received;
  Stop the asynchronous scan timer;
  Set scan channel list to the synchronous scan channel list.

In one embodiment, the state diagrams of FIGS. 7 and 8 are implemented in system 100, including its specific embodiment system 200. The state diagram of FIG. 7 is implemented using telemetry controller 446 of telemetry circuit 222. The state diagram of FIG. 8 is implemented using telemetry controller 446 of telemetry circuit 220. These state diagrams are discussed using various scenarios below.

Scenarios for Sending and Receiving Data from the IMD

There are several different scenarios for sending data to the IMD (the forward channel) and retrieving data from the IMD (the reverse channel). For each scenario, the PRM and the IMD operate to re-establish a communication link. In the following discussion of these scenarios, programmable values for timer periods and hop counts have been set to the following nominal values: Primary Channel Timer 150 ms; Synchronous Scan Timer=25 ms; Asynchronous Scan Timer=25 ms; Synchronous Scan Hop Count=80 counts; and PRM polling interval=100 ms. These values are examples only, and do not necessarily represent the only or optimal set of values.

Scenarios for Normal Operation
Normal Operation for Data Inbound to the IMD (Forward Direction)

In this scenario, the frame exchange operates normally and there is no error in the exchange of any frame. The PRM sends the DS (data send) frame to the IMD, and the IMD successfully receives the frame and replies with the ACK. The IMD, upon completion of transmitting the ACK, resets the Primary Channel Timer. In this scenario, the two Primary Scan Timers are expected to be within a few hundred microseconds of each other.

Normal Operation for Data Outbound from the IMD (Reverse Direction)

In this scenario, the frame exchange operates normally and there is no error in the exchange of any frame. The PRM sends the CTS (clear to send) frame to the IMD. The IMD successfully receives the frame and replies with the DS. The PRM responds with the ACK and upon completion of transmitting the ACK, resets the Primary Channel Timer. In this scenario, the two Primary Scan Timers are expected to be within a few hundred microseconds of each other, according to various embodiments.

Failure Scenarios: Data Transfer from the IMD
IMD Fails to Receive the CTS on an Inbound Exchange On the previous exchange, both the PRM and the IMD reset the primary timer on the ACK and the two timers should be very close to one another. At the poll interval the PRM sends a CTS but the IMD does not receive the frame. The PRM having not received the start of the DS frame will retry the exchange by transmitting the CTS 1 ms after the previous CTS was transmitted, alternating antennas on dual antenna systems according to varying embodiments. The PRM will continue transmitting CTS frames on alternating antennas until the Primary Channel Timer expires. Since both the PRM and the IMD had reset the Primary Channel Timers based on the last successful transmit/receive of an ACK frame (see scenarios 1 and 2 above), the IMD Primary Channel Timer will also expire at very nearly the same time. Using the values suggested above, the timers will expire 150 ms after the last ACK, assuming a maximum sized DS frame (a 10 ms exchange) in the previous exchange, this will be 60 ms into the polling interval (150 ms primary channel timer+10 ms exchange−100 ms poll interval=60 ms). At this time, the IMD moves to the next channel in the synchronous scan list and the PRM begins scanning the next 9 channels, C1 to C9, according to an embodiment. The PRM continues to scan the same 9 channels, C1 to C9, for 100 ms. Each scan of the 9 channels takes 25 ms, so after 100 ms each channel has been tried 4 times on each antenna for a total of 8 tries per channel. The IMD, having not transmitted or received an ACK frame on any of the channels, will have hopped 4 channels within this 100 ms and will be on channel C5, according to an embodiment. The PRM begins modifying its scan list on every synchronous timer expiration, by dropping the first channel in the list and adding a next channel from the synchronous scan list to the end of the scan. The result is that the PRM keeps a window of scanned channels around where the IMD is most likely to be trying (C5 between C2 and C10, in this example). If the PRM finds the IMD on the first channel hop (C1), a complete data exchange is executed within 70 ms, or 60 ms into the existing polling period plus 10 ms for the data exchange. Assuming a 100 ms polling interval, this would be completed 170 ms after the last valid exchange.

PRM Fails to Receive the Start of the DS Response from the IMD

On the previous exchange, both the PRM and the IMD reset the primary timer on the ACK and the two timers should be very close to one another. The PRM sent a CTS frame to the IMD, and the IMD responds with the DS frame but the start of the frame is not identified by the PRM. The PRM then transmits the CTS frame again 1ms after the original CTS frame. Both the PRM and the IMD are transmitting simultaneously. The DS frame from the IMD can take up to 8.2 ms (max DS frame), so that the first 9 CTS retries from the PRM will be in vain. The tenth retry will be the next attempt when the IMD will be listening. With a 150 ms timeout, this will allow 60 CTS retries (150 ms timeout−100 ms poll interval+10 ms longest previous exchange=60 ms) from the PRM, of which at least 6 attempts are certain to be when the IMD is listening. Since no ACK frames were transmitted or received, both primary channel timers will expire very close in time to one another. The PRM and the IMD will enter synchronous scan timer mode, and the scan will follow the same pattern as in the scenario above.

PRM Receives the Start of the DS Frame but Cyclic Redundancy Check (CRC) Fails

This is similar to scenario (4) above except that, since the PRM did receive the start of the DS frame, it will not be transmitting at the same time as the IMD. As no ACK frames were transmitted or received, the two primary channel timers expire very close in time to one another. According to this embodiment, there is still time for 6 attempts (two per antenna) at a full data exchange rate.

IMD Fails to Receive the ACK

In this scenario, the PRM and the IMD primary channel timers are skewed by a significant amount. The PRM sends the CTS, the IMD responds with the DS, and the PRM responds with the ACK, but the IMD does not receive the ACK frame. The PRM having sent the ACK will reset the primary channel timer back to 150 ms. The IMD not having received the ACK will not reset its primary channel timer. The PRM, thinking that the exchange was a success, will go to sleep and wakeup to poll the IMD 100 ms after the start of the failed poll. The PG primary channel timer will expire 60 ms into the polling period and enter synchronous scan mode. With 40 ms left in the poll interval the IMD will have hopped 2 channels (C2) prior to the PRM waking up. The PRM wakes up and polls on channel C0 for 60 ms until its primary channel timer expires sending the PRM into synchronous scan mode. In this 60 ms, the IMD will have hopped an additional two channels and will be at channel C4 with the PRM begins scanning. The PRM will be scanning C1-C9 for the first 25 ms making the IMD (at C4) right in the middle of the channels scanned. In this failure mode, the PRM will start modifying the channel list after each of the passes through the list of 9 channels.

Failure Scenarios: Data Transfer to the IMD
PG Fails to Receive a DS Frame

In this scenario, the PRM is sending DS frames to the IMD. The IMD does not receive the DS, so no ACK is sent back to the PRM. Without the IMD having sent an ACK, neither the PRM nor the IMD resets its primary channel timer. The PRM attempts the DS frame until the primary channel timer expires. The PRM retries for the first 60 ms of the polling interval, when the primary channel timer expires. Since no ACK was sent or received, the primary channel timers will expire very close in time to one another. From the PRM perspective, this scenario cannot be distinguished from the scenario below. The PRM waits 210 ms prior to modifying the synchronous scan list. When both sides begin to scan, the PRM will have a scan list of C1 to C9 and the IMD will be at C1 (on the PRM scan list). In the worst case, after 210 ms of waiting the IMD will have hopped an additional 8 channels and be at C9, while the PRM will modify its scan list to C2 to C10 such that C9 is still on the PRM scan list.

IMD Sends an ACK, but PRM Fails to Receive it

The IMD having received a valid DS frame sends an ACK frame and resets its primary channel timer. The PRM, having failed to receive the ACK, does not reset its primary timer. The PRM will continue to retry the DS frame until the primary channel timer expires. This allows a minimum of 6 retries before the PRM begins scanning for a new channel 60 ms into the polling interval. The IMD, however, has reset its primary channel timer each time it sent an ACK frame, which may be to all 6 DS attempts. The IMD will begin scanning no earlier than after the first DS ACK (10 ms into the polling interval) and as much as after the 6 DS ACK exchanges (60 ms into the polling interval) for a range of 160 ms to 210 ms. The PRM could be scanning for at least 160 ms and up to 210 ms prior to the IMD hopping to C1. In this case, the PRM should not begin to modify its scan list for 210 ms which would allow the IMD to have begun hopping at C1 and may have already hopped as many as 3 channels to C3. When the PRM starts hopping its list of channels to scan will be from C1 to C9, so that the IMD being on C1 or C3 will be in the PRM scan list.

Scenarios for Operation in Scan Mode

There are several scenarios for operation in synchronous scan mode and asynchronous scan mode. For each scenario, the PRM and the IMD operate in scan mode and transition back to primary mode. In the following discussion of these scenarios, programmable values for timer periods and hop counts have been set to the nominal values discussed above.

A Successful SCAN Exchange has Occurred and the NODATA-ACK Exchange Works

This embodiment is the normal case for transitioning from the synchronous scan mode and the asynchronous scan mode back to primary mode. The PRM sends the SCAN to the IMD and the IMD replies with the SCAN frame, and the PRM receives the SCAN response with no errors. At this time, the PRM knows what frequency the IMD is currently listening on ($C_s$), so it modifies the scan list to put the channel that the SCAN exchange worked on as the first channel in its list of channels to continue to scan. The scan list for the PRM will now be $C_s$ to $C_{s+8}$. This is an intermediate synching of the scan lists. The PRM then sends the NODATA frame to the IMD and the IMD receives the frame without errors. The IMD responds to the NODATA frame with the ACK frame. At this time, the IMD returns to primary channel mode. Since the IMD sent an ACK, it resets its primary channel timer at the end of the ACK transmission. The PRM receives the ACK frame successfully and then resets its primary channel timer and enters primary mode.

A Successful SCAN Exchange has Occurred, the IMD Responds with the ACK Frame but the PRM Fails to Receive the ACK Frame The PRM sends the SCAN to the IMD, the IMD replies with the SCAN frame, and the PRM receives the SCAN response with no errors. At this time, the PRM knows what frequency the IMD is listening on, so it modifies the scan list to put the channel that the SCAN exchange worked on as the first channel in its list of channels to continue to scan, and will use this channel if more SCAN exchanges are required. The scan list for the PRM will now be $C_s$ to $C_{s+8}$. This is an intermediate synching of the scan lists. The PRM then sends the NODATA frame to the IMD and the IMD receives the frame without errors. The IMD responds to the NODATA frame with the ACK frame. At this time, the IMD returns to primary channel mode. Since the IMD sent an ACK, it resets its primary channel timer at the end of the ACK transmission. The IMD will not hop frequencies at this point for the primary channel timeout of 160 ms. To match this, the PRM prohibits changing of channels for at least 210 ms after the successful exchange of the SCAN. The PRM fails to receive the ACK frame successfully, so it transmits a subsequent SCAN frame after the SCAN timeout expires. Since the PRM modified the scan list, the first channel the SCAN is sent on is the same channel as the previous SCAN exchange worked on. The IMD will also be on this same channel. The IMD will respond with the SCAN frame, the NODATA from the PRM will result in an ACK from the IMD, and both sides will be in primary mode with the primary channel timers substantially synchronized. In cases where the PRM continues to have failures in the SCAN response or the ACK response, the two sides will begin hopping frequencies with the IMD at $C_s+_2$ and the PRM at $C_s$ after the primary channel timers expire.

A Successful SCAN Exchange has Occurred, and the IMD Fails to Receive the NODATA In this scenario, neither side has transmitted or received an ACK, so neither will enter primary mode. In this embodiment, the PRM will have synched the scan list to start with $C_s$ and will not hop channels for 210 ms. The worst case would allow for the IMD to hop 8 channels to $C_s+_8$ in this time, so the IMD channel will still be on the PRM scan list of $C_s$ to $C_s+_8$. Any successful SCAN exchange will sync the scan list again.

The PRM Fails to Receive the SCAN Response from the IMD

The PRM sends a SCAN frame and the IMD responds with a SCAN frame but the PRM does not receive it. Neither side has sent a NODATA or ACK frame, so after the synchronous scan timer or asynchronous scan timer expires, the two sides will hop to the next channel on the list.

The IMD Fails to Respond to the SCAN Frame

Neither side has sent a NODATA or ACK frame, so after the synchronous scan timer or asynchronous scan timer expires, the two sides will hop to the next channel on the list.

Although specific embodiments have been illustrated and described herein, it will be appreciated by those of ordinary skill in the art that any arrangement which is calculated to achieve the same purpose may be substituted for the embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

We claim:

1. A system, comprising:
    an implantable medical device including:
        a therapy module; and
        an implant telemetry module; and
    an external system, including:
        a programming module; and
        an external telemetry module,
    wherein the implant telemetry module and the external telemetry module each include a telemetry circuit including:
        an antenna;
        a transceiver coupled to the antenna, the transceiver adapted to transmit over a plurality of channels each representing a predetermined frequency band for data transmission between the implantable medical device and the external system; and
        a telemetry controller coupled to the transceiver, the telemetry controller adapted to control a channel hopping process including detecting failure of a communication session on a first frequency, synchronously scanning a subset of available channels included in a synchronous scan list for a response from the implantable medical device when the failure is detected, resuming the communication session with the implantable medical device after receiving a response, on a second frequency on which the response was received, and asynchronously scanning available channels when no response is received during synchronous scanning.

2. The system of claim 1, wherein the telemetry controller is further adapted to select an active channel from the plurality of channels, to control the data transmission using the active channel during a synchronous scan mode during which the channel hopping in the external system and the channel hopping in the implantable medical device are synchronous, to start an asynchronous scan mode after the channel hopping in the external system and the channel hopping in the implantable medical device become asynchronous, and to restore the synchronization of the channel hopping in the external system and the channel hopping in the implantable medical device during the asynchronous scan mode.

3. The system of claim 1, wherein the therapy module includes CRM module.

4. The system of claim 1, wherein the therapy module comprises a sensing circuit adapted to sense one or more physiological signals.

5. The system of claim 3, wherein the CRM module comprises a therapy circuit adapted to deliver cardiac electrical stimulation pulses.

6. The system of claim 1, wherein the therapy module includes neurostimulation module.

7. The system of claim 1, further comprising a memory electrically connected to the controller, the memory adapted to store available communication frequencies and timers for synchronous and asynchronous scanning of frequencies.

8. The system of claim 7, wherein the memory includes a primary channel timer storage location.

9. The system of claim 7, wherein the memory includes a synchronous scan timer storage location.

10. The system of claim 7, wherein the memory includes an asynchronous scan timer storage location.

11. The system of claim 7, wherein the memory includes a synchronous scan hop count storage location.

12. The system of claim 7, wherein the memory includes a polling interval storage location.

13. A method, comprising:
    communicating wirelessly with an implantable medical device using a first frequency until failure of a communication session is detected on the first frequency;
    synchronously scanning a subset of available channels according to a synchronous scan list for a response from the implantable medical device when the failure is detected;
    resuming the communication session with the implantable medical device after receiving a response, on a second frequency on which the response was received; and
    asynchronously scanning available channels when no response is received during synchronous scanning.

14. The method of claim 13, further comprising:
    incrementing the subset of available frequencies after a programmable time period.

15. The method of claim 14, wherein incrementing the subset of available frequencies includes dropping a first available frequency from a beginning of the subset and adding a next available frequency to an end of the subset.

16. The method of claim 15, wherein incrementing the subset of available frequencies ensures that frequencies scanned by the implantable medical device remain among the subset.

17. The method of claim 13, further comprising:
    resetting a hopping clock timer internal to the implantable medical device to maintain synchronization between the implantable medical device and a second device.

18. A system, comprising:
    means for communicating wirelessly with an implantable medical device using a first frequency until failure of a communication session is detected on the first frequency;
    means for synchronously scanning a subset of available channels according to a synchronous scan list for a response from the implantable medical device when the failure is detected;
    means for resuming the communication session with the implantable medical device after receiving a response, on the frequency which the response was received; and
    means for asynchronously scanning available channels when no response is received during synchronous scanning.

19. The system of claim 18, wherein the communicating means includes at least one antenna.

20. The system of claim 18, wherein the communicating means includes a controller and a memory.

* * * * *